United States Patent [19]

Nagata et al.

[11] Patent Number: 4,791,655
[45] Date of Patent: Dec. 13, 1988

[54] METHOD AND APPARATUS FOR THE INSPECTION OF CONTENTS OF PACKAGED PRODUCTS

[75] Inventors: Masanori Nagata; Shigeki Imano; Tsugio Kaneoka; Kiyotoshi Asada, all of Tokyo, Japan

[73] Assignee: Fujimori Kogyo Co., Ltd., Tokyo, Japan

[21] Appl. No.: 137,687

[22] Filed: Dec. 24, 1987

[30] Foreign Application Priority Data

Dec. 29, 1986 [JP] Japan ................ 61-310948
Apr. 29, 1987 [JP] Japan ................ 62-105749

[51] Int. Cl.⁴ .................................. G01N 23/06
[52] U.S. Cl. ............................ 378/57; 378/51
[58] Field of Search ...................... 378/51-54, 378/57, 58, 62

[56] References Cited

U.S. PATENT DOCUMENTS 3,007,048 4/1988 Knapp et al. ............ 378/58
3,995,164 11/1976 Ramsay et al. ........... 378/51

FOREIGN PATENT DOCUMENTS 3320314 12/1983 Fed. Rep. of Germany ........ 378/53
57-69235 4/1982 Japan ................ 378/51

Primary Examiner—Craig E. Church
Assistant Examiner—Joseph A. Hynds
Attorney, Agent, or Firm—Armstrong, Nikaido, Marmelstein & Kubovcik

[57] ABSTRACT

There is disclosed an apparatus and method for inspecting the contents, such as food, of a package, particularly a light-opaque package, for degradation or the degree of degradation by means of ultra-soft X-rays. The inspection apparatus generally comprises a shaking unit for shaking the package and a main inspecting unit disposed downstream and independently of the shaking unit. The assessment of degradation of the degree of degradation can be made according to the state of dispersion, after shaking, of the package head space in the X-ray image information. The method and apparatus eliminate losses arising from destructive inspection.

6 Claims, 3 Drawing Sheets

METHOD AND APPARATUS FOR THE INSPECTION OF CONTENTS OF PACKAGED PRODUCTS

BACKGROUND OF THE INVENTION

The present invention relates to a method for inspecting the contents, such as food, of a package, particularly a light-opaque package, for degradation or the degree of degradation by means of ultra-soft X-rays (which is generally referred to briefly as soft X-rays) and an apparatus for use in practicing the method.

It is an important element of quality control, in some industries, to check the contents of packaged products, such as food contained in a pouch or other packaging container, for degradation.

In case the degradation of contents is accompanied by the evolution of gases within the package, one may readily discover the occurrence of degradation from the inflation of the container. If the container is a transparent or see-through pouch, for instance, signs of degradation can be easily detected by looking through the pouch.

These procedures are of no avail, however, where a light-opaque packaging material such as an aluminum foil-laminated film is used for purposes of an improved shelf-life, where the contents are such that they will not give rise to gases on decomposition, or where the degradation of the contents has not progressed far enough to cause gas production.

Therefore, in such cases, it has been inevitable to pick up an appropriate number of samples, destroy them, and check the contents by visual inspection.

However, the destructive inspection of packaged products is disadvantageous in that the procedure involves many steps and the sampled products, if acceptable, become loses on account of unpackaging, thus adding to the cost of products. Furthermore, while an unfailing inspection calls for many samples, there is naturally a limit to sampling size, with the result that the reliability of the inspection is compromised.

It is an object of the present invention to provide a method of inspecting packaged products, by which the contents, such as food, of a light-opaque package can be accurately checked for degradation or the degree of degradation without destroying the packaging container. Another object is to provide an apparatus for use in practicing the method.

SUMMARY OF THE INVENTION

The inspection method according to the present invention comprises shaking a package 1, which is a packaging container 1a containing fluid contents 1b, irradiating said package 1 with ultra-soft X-rays from outside thereof to give an image information, and assessing the occurrence or non-occurrence of degradation or the degree of degradation of said contents 1b according to the state of dispersion of the package head space in said image information.

The inspection apparatus according to the present invention is adapted to shake a package 1, which is a packaging container 1a containing fluid contents 1b, and irradiate the package 1 from outside thereof with ultra-soft X-rays for assessment of the occurrence or non-occurrence of degradation or the degree of degradation of said contents 1b.

As such, the apparatus of the present invention generally comprises a shaking unit 2 for shaking the package 1 and a main inspecting unit 3 disposed downstream and independently of said shaking unit 2, said shaking unit 2 comprising a first conveyer belt 21 for carrying said package 1 and conveying it in a downstream direction, a shaking device 22 for shaking said package 1 in transit and a retaining belt 23 disposed in parallel with said first conveyer belt 21 for supporting the package 1 in transit, and said main inspecting unit 3 comprising a second conveyer belt 31 for receiving the package 1 from said first conveyer 21 of shaking unit 2 and conveying the same in a downstream direction, an ultra-soft X-ray irradiation device 32 for irradiating said package 1 on said second conveyer 21 with ultra-soft X-rays, and an image display device 33 for displaying an image information from the irradiated package 1, whereby the contents 1b of the package 1 may be checked for the occurrence or non-occurrence of degradation or the degree of degradation according to the state of dispersion of the package head space in the image information.

Inspection procedures utilizing ultra-soft X-rays have heretofore been applied to the detection of contamination of products with foreign matter in the food and related industries but it is believed that it has not been known to evaluate the quality of packaged products in terms of degradation of contents according to the state of dispersion of package head space in an ultra-soft X-ray image information from the package.

DETAILED DESCRIPTION OF THE INVENTION

Figure 1:
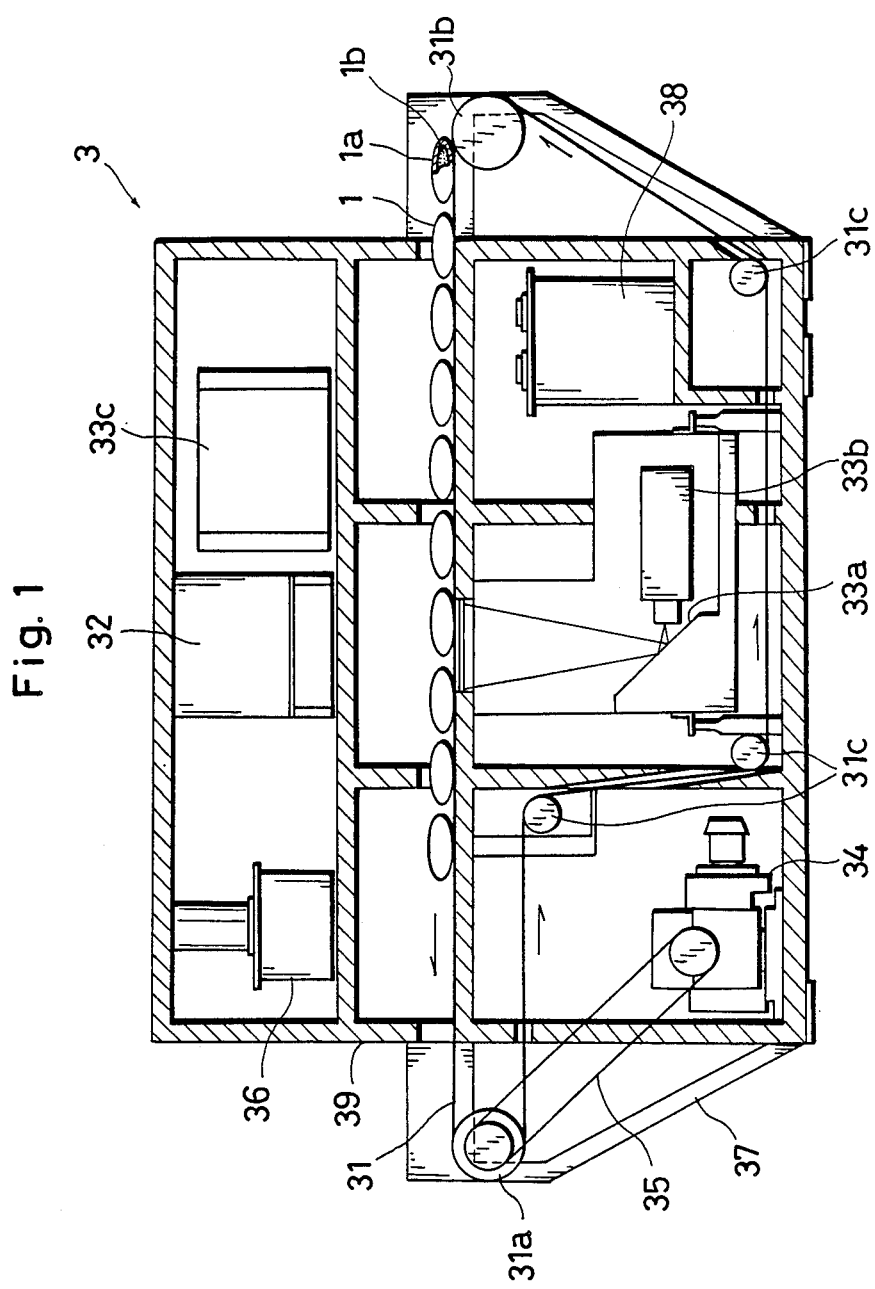
FIG. 1 is a cross-section view showing an exemplary main inspecting unit 3 in the inspection apparatus according to the present invention.

The present invention is described in detail below.

The packaging material for the packaging container 1a is generally a flexible packaging material, such as a single-layer or multiple-layer plastic packaging material, a composite packaging material manufactured by laminating a plastic sheet with a metal foil, a metal-deposited film or paper, or a packaging material manufactured by coating or otherwise cladding a fabric web of natural or synthetic fiber with synthetic resin, at least the innermost layer of said packaging material being a heat-bondable.

As examples of said packaging container 1a, there may be mentioned a variety of pouches, bottles, bags, bag-in-boxes, tubes, laminated tubes, milk cartons, composite cans, metal cans and so on.

As to the form of said packaging container 1a, taking the pouch as an example, it may be a trianglar pouch, a gasset pouch, a self-standing pouch or the like. Thus, there is no limitation on the shape of the packaging container. It is essential, however, that after filling with contents 1b, there should be a residual gas space, that is to say a head space, within the container 1a.

As examples of contents 1b which are filled into the packaging container 1a, there may be mentioned various foodstuffs, pharmaceutical products, feedstuffs, and so on. Particularly important are foodstuffs. There is no limitation on the type or consistency of contents 1b except that they must be fluids such as solutions, homogeneous dispersions, pastes and so on.

The packaging material 1a is filled with contents 1b to provide the package 1.

In inspecting the package 1 in accordance with the present invention, the package 1 is first shaken either mechanically, manually, or ultrasonic vibration. By this shaking procedure, the head space (the internal space other than the contents) within the package is dispersed according to the viscosity of the contents and other conditions.

Then, the package 1 is irradiated with ultra-soft X-rays from outside in the above condition, whereby an image information is obtained. This image information may be any of fluorescence image (transmission or TV image), negative film image (X-ray photograph) and PbO-TV image. The fluorescence image and film image are usually obtained as life-size images, while the PbO-TV image as an enlarged image on a monitor screen.

By observing the state of dispersion of said head space in the above-mentioned image, the occurrence or non-occurrence of degradation or the degree of degradation can be easily ascertained or evaluated, for when there is no degradation, the degree of dispersion of the head space is low, while when there is degradation the number of divided head spaces is greater with an increasing degree of degradation.

The inspection apparatus according to the present invention comprises a shaking unit 2 for shaking the package 1 and a main inspecting unit 3. The main inspecting unit 3 is disposed downstream and independently of the shaking unit 2.

The assembling of the shaking unit 2 with the main inspecting unit 3 as an integral setup should be avoided, for otherwise the vibrations of the shaking unit 2 are transmitted to the main inspecting unit 3 so that the X-ray beam from the ultra-soft X-ray irradiation device 32 goes out of focus on the vibrating package 1 to blur the image projected on the image display device 33.

The shaking unit 2 comprises a first conveyer belt 21, a shaking machine 22, a retaining belt 23, and members ancillary to these element and devices.

The first conveyer belt 21 is adapted to convey the package 1 in a downstream direction. The first conveyer belt 21 may be provided with dams 24 spanning the width thereof so that a row of packages 1 may be independently positioned between dams 24 and conveyed.

The shaking device 22 is adapted to shake the package 1 traveling with the first conveyer belt 21. The shaking device 22 may be of any known construction, such as a device adapted to transform the rotary motion of a motor into a sinusoidally linear movement by means of a crankshaft and a rod, a device utilizing the attractive force of an electromagnet, a device employing a vibration motor (a motor having a drive shaft fitted with imbalance weights at both ends is driven to generate a centrifugal force), a device employing a mechanical vibrator or a device using an ultrasonic vibrator.

The retaining belt 23 is adapted to support the traveling package 1 in cooperation with the first conveyer belt 21 and disposed in parallel with the first conveyer belt 21. The retaining belt 23 is preferably so designed that it is able to advance or retreat with respect to the first conveyer belt 21 and, upon contact with the package 1, is allowed to follow the movement of the package 1. The retaining belt 23 is preferably made of an elastic material.

The main inspecting unit 3 mentioned hereinbefore comprises a second conveyer belt 31, an ultra-soft X-ray irradiation device 32, an image display device 33, and members ancillary to such element and devices.

The second conveyer belt 31 is adapted to receive the package 1 from the first conveyer belt 21 of the shaking unit 2 and convey the package 1 further in a downstream direction. This second conveyer belt 31 need not be provided with partitioning means such as the dams mentioned hereinbefore. The width of the second conveyer belt 31 is generally equal to that of the first conveyer belt 21, although a minor difference is tolerated.

The ultra-soft X-ray irradiation device 32 is adapted to irradiate the package 1 on the second conveyer belt 31 with ultra-soft X-rays. The term 'ultra-soft X-rays' as used herein means X-rays in the wavelength range close to ultraviolet rays, which are in contrast with the usual X-rays in the wavelength range close to gamma-rays. The ultra-soft X-rays are sometimes referred to simply as soft X-rays.

The image display device 33 is adapted to display the X-ray image of the irradiated package 1.

The image display device 33 is preferably a system (a) comprising a fluorescent image-forming plate 33a, a fluorescent image photographing camera (CCTV) 33b and a television receiver 33c or a system (b) comprising a transmission soft X-ray photographing camera (PbO-TV) 33d and a television receiver 33c.

In the former system (a), the transmission X-ray image of the package 1 is formed as a fluorescent image on the fluorescent image-forming plate 33a and this X-ray image is photographed by CCTV 33b and projected on the CRT screen of the television receiver 33c.

In the latter system (b), the transmission X-ray image is photographed by the PbO-TV 33d and displayed on the screen of the TV receiver 33c.

Comparing system (a) with system (b), the former is advantageous over the latter in terms of equipment cost while system (b) is superior to system (a) in the resolution of images.

In the inspection apparatus according to the present invention, there is preferably provided, at the downstream end of the second conveyer belt 31 of the main inspecting unit 3, a sorting device 4 for discharging packages 1 found defective in isolation from packages 1 found acceptable.

The sorting device 4 may for example be one of the following devices.

Figure 4:
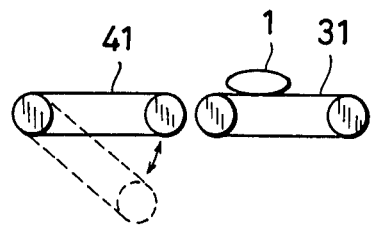
FIGS. 4 through 6 are explanatory views each illustrating an exemplary sorting mechanism 4.

(1) As shown in FIG. 4, a third conveyer belt 41 is installed at the downstream end of the second conveyer belt 31 of the main inspecting unit 3 in such a manner that one end of said third conveyer belt 41 is vertically movable, so that when a package 1 found defective has moved onto the third conveyer belt 41, said end of the belt 41 is lowered to discharge the defective package 1.

Figure 5:
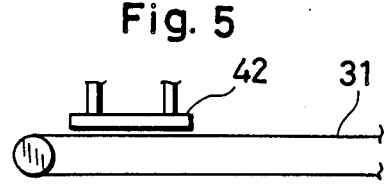

(2) As illustrated in FIG. 5, the downstream end of the second conveyer belt 31 of the main inspecting unit 3 is provided with a sweeping means 42 so that the package 1 found defective may be sweped away in a lateral direction of the second conveyer belt 31.

Figure 6:
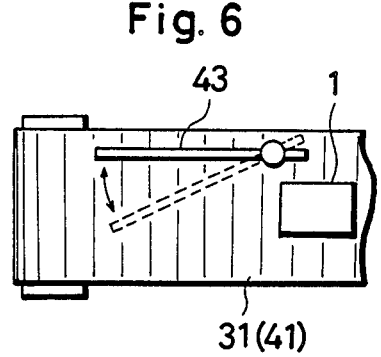

(3) As illustrated in FIG. 6, a guide rail 43 is installed at the downstream end of the second conveyer belt 31 of the main inspecting unit 3 or over the third conveyer belt 41 associated therewith and the direction of this guide rail 43 is controlled to guide the package 1 found defective in a path different from the path of travel of the package 1 found acceptable.

In order to inspect a package 1, which is a packaging container 1a containing contents 1b, the package 1 is fed to the upstream end of the first conveyer belt 21 of the shaking unit 2 so that the package 1 may travel toward the downstream end of the belt 21.

The package 1 travels as sandwitched between the first conveyer belt 21 and retaining belt 23 and, in the course of this travel, is shaken by the shaking unit 22. By this shaking operation, the head space within the package 1 is dispersed into the contents 1b.

The shaken package 1 is then transferred from the first conveyer belt 21 of the shaking unit 2 to the second conveyer belt 31 of the main inspecting unit 3, by which it is conveyed in a downstream direction.

The package 1 on the second conveyer belt 31 ceases to be vibrated at the upstream end of the second conveyer belt 31 and the head space dispersed into the contents 1b rises or coalesces owing to its buoyancy according to the viscosity of the contents 1b.

When the package 1 on the second conveyer belt 31 reaches the irradiation zone of the ultra-soft X-ray irradiation device 32, it is exposed to ultra-soft X-rays and the resultant transmission X-ray image is displayed on the screen of the image display device 33.

The difference between the transmission power of ultra-soft X-rays and the absorbancy of the material, that is to say the transmission differential on the fluorescent plate or film, produces a density gradient image. The absorption of ultra-soft X-rays is greater with a substance of high density or thickness, and the long-wavelength soft X-rays show a pattern of transmission corresponding to the density distribution, yielding a well-contrasted sharp transmission image of good resolution.

When the contents 1b, such as food, are degraded or spoiled, there occurs a change in density or a coagulation and as a result, when the package 1 is shaken, the head space in the package 1 is dispersed in a manner different from the dispersion occurring in a wholesome package so that the degree of degradation can be assessed from the ultra-soft X-ray image information.

Therefore, based on the state of dispersion of the head space on the image of package 1 displayed by the image display unit 33, the inspector can render a judgement as to whether there is degradation or not or assess the degree of degradation and operate the sorting device 4 for culling out defective product packages.

In operating the apparatus of the invention, the shaking time is generally set at 1 to 40 seconds, the shaking amplitude at 1–40 mm, the shaking cycle at 1 to 15 times/second, and the standing time (time from shaking to determination) at 5 to 60 seconds.

By means of the apparatus according to the present invention, the packaged contents 1b can be accurately checked for degradation without destroying the package 1, so that there are realized many advantages. Among such advantages are: the degree of degradation can also be evaluated, the number of inspection steps can be drastically reduced as compared with the destructive inspection, quick checking is possible, and the sampling size may be increased and even an inspection of all items can be carried out. Thus, the invention is of great industrial value, particularly in the food industry.

Another advantage of the invention is that, notwithstanding the use of X-rays, neither control zone designation nor the special qualification of inspecting personnel is required.

EXAMPLES

The following examples are further illustrative of the present invention.

Example 1

Hardware Layout

FIG. 1 is a cross-section view showing an exemplary main inspecting unit 3 in the inspecting apparatus according to the invention.

Figure 2:
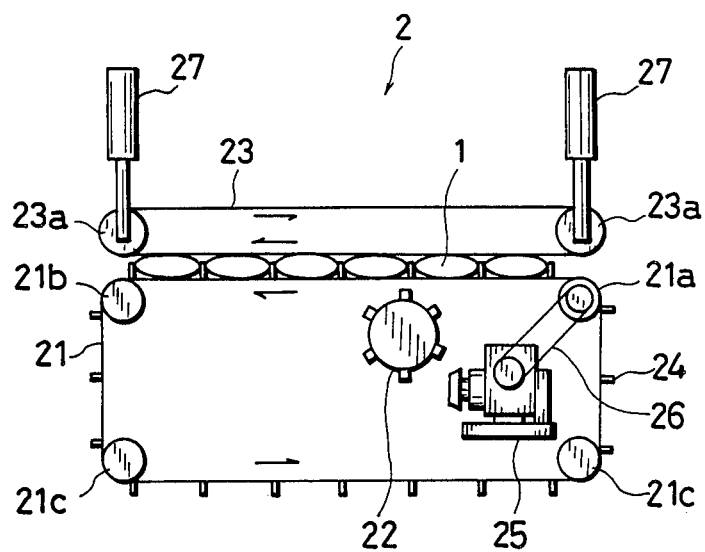
FIG. 2 is a schematic view showing the main part of an exemplary shaking unit (2) in the inspection apparatus of the invention.

FIG. 2 is a schematic view showing the main part of an exemplary shaking unit 2 in the inspecting apparatus according to the invention.

The shaking unit, indicated generally at 2, comprises a first conveyer belt 21, a shaking device 22 and a retaining belt 23.

The first conveyer belt 21 is driven by a drive roll 21a. The reference numeral 25 represents a motor for driving said drive roll 21a, 26 a drive belt installed between said motor 25 and drive roll 21a, 21b a driven roll, and 21c a guide roll.

The reference numeral 24 represents dams on the first conveyer belt 21 and each package 1 is set in position between dams 24 and conveyed.

The shaking device 22 is disposed in an intermediate position of the first conveyer belt 21 and imparts a shaking motion to the first conveyer belt 21.

The retaining belt 23 is installed between rolls 23a and 23a over and in parallel with the first conveyer belt 21 in such a manner that it is caused to advance or retreat with respect to the first conveyer belt 21 by hydraulic means 27 and 27.

The reference numeral 3 represents a main inspecting unit which comprises a second conveyer belt 31, an ultra-soft X-ray irradiation device 32 and an image display device 33.

The second conveyer belt 31 is driven by a drive roll 31a. The reference numeral 34 represents a motor for driving said drive roll 31a, 35 a drive belt installed between said motor 34 and drive roll 31a, 31b a driven roll, and 31c . . . are guide rolls.

The ultra-soft X-ray irradiation device 32 is installed over and substantially in the center of the second conveyer belt 31.

The image display device 33, in this Example 1, is a system comprising a fluorescent image-forming plate 33a, CCTV 33b and a television receiver (video monitor) 33c.

Referring to the main inspecting unit 3, the reference numeral 36 represents a cooling unit, 37 a protective plate, 38 a high-tension transformer, and 39 a frame.

The sorting device 4 may be any of the devices illustrated in FIGS. 4 through 6 but is not shown in FIG. 1.

Sample

A packaging pouch (an example of packaging container 1a) made of a 4-layer laminate material consisting, in the order from the outermost layer to the innermost layer, of 12 $\mu$m-thick polyester film, 9 $\mu$m-thick aluminum foil, 15 $\mu$m-thick biaxially oriented nylon film and 70 $\mu$m-thick polyethylene film was filled with 200 ml of a potage (an example of contents 1b) and sealed to give a sample package 1. As samples of the potage, one immediately following preparation (hereinafter referred to as non-degraded soup), one allowed to stand at room temperature for 4 or 5 days after preparation (hereinafter referred to as short-term degradated soup), and one allowed to stand at room temperature for 2 weeks (hereinafter referred to as long-term degraded soup) were used.

Test

Using the ultra-soft X-ray irradiator SV-100A (maximum output 100 kV$_p$·5 mA, full wave rectification type) manufactured by Softex Corporation as the ultra-soft X-ray irradiation device 32 in the above apparatus, the degrees of degradation of the above sample packages 1 were determined under the following conditions: shaking time (retention time on first conveyer belt 21)=5 seconds; standing time (the time on second conveyer belt 31 till the irradiation zone of the ultra-soft X-ray irradiator is reached)=30 seconds.

Visual inspection of the image projected on the screen of the TV receiver 33c revealed that whereas, in the case of non-degraded soup, the head space images were localized substantially in one position, with only a few small images being scattered, there was a large number of dispersed head space images, with the individual images being larger and varying in size, in the case of short-term degraded soup. Further, in the case of long-term degraded soup, the head space images were more numerous and divergent in size. The differences among the non-degraded soup, short-term degraded soup and long-term degraded soup were obvious at a glance.

Example 2

Apparatus

Figure 3:
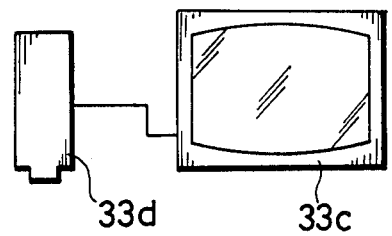
FIG. 3 is an explanatory view showing an image display device 33 in another embodiment of the inspection apparatus according to the invention.

FIG. 3 is an explanatory view showing the image display device 33 as another example of the inspecting apparatus according to the present invention.

The image display device 33, in this Example 2, is a system in which the transmission X-rays are photographed by PbO-TV 33d and projected on the screen of the TV receiver 33c.

Sample

A packaging pouch (an example of the packaging container 1a) made of a 3-layer laminate material consisting, in the order from the outermost layer to the innermost layer, of 12 μm-thick polyester film, 9 μm-thick aluminum foil and 80 μm-thick unoriented polypropylene film was filled with 200 ml of white sauce (an example of contents 1b) and sealed to give a sample package 1. As samples of the white sauce, one immediately following preparation (hereinafter referred to as non-degraded sauce) and one allowed to stand at room temperature for 1 week after preparation (hereinafter referred to as intermediate-term degraded sauce) were used.

Test

Using the above-mentioned apparatus and sample packages, the degradation assessment test was performed under the same conditions as Example 1.

Visual inspection of the images projected on the screen of the TV receiver 33c revealed that whereas the head space images of non-degraded sauce were localized substantially in one position, with only a few small discrete images being scattered, the intermediate-term degraded sauce showed a larger number of dispersed head space images with the individual images being larger in size. Thus, the difference between the images of the two products was obvious at a glance.

What is claimed is:

1. A method of inspecting packaged products which comprises shaking a package (1) containing fluid contents (1b) in a packaging container (1a), irradiating the package 1 with soft X-rays from outside thereof to obtain an image information, and assessing the occurrence or non-occurrence of degradation or the degree of degradation of contents (1b) according to the state of dispersion of package head space in the image information.

2. An inspection method according to claim 1 wherein said contents are food.

3. A packaged product inspection apparatus for assessing the occurrence or non-occurrence of degradation or the degree of degradation of fluid contents (1b) in a packaging container (1a) by shaking a package (1) and, then, irradiating it with soft X-rays from outside thereof, which apparatus comprises a shaking unit (2) for shaking the package (1) and a main inspecting unit (3) disposed downstream and independently of said shaking unit (2), said shaking unit (2) comprising a first conveyer belt (21) for conveying said package (1) in a downstream direction, a shaking device (22) for shaking said package (1) in transit and a retaining belt (23) disposed in parallel with said first conveyer belt (21) for supporting the package (1) in transit, and said main inspecting unit (3) comprising a second conveyer belt (31) for receiving the package (1) from said first conveyer (21) of shaking unit (2) and conveying the same in a downstream direction, a soft X-ray irradiation device (32) for irradiating said package (1) on said second conveyer (21) with soft X-rays, and an image display device (33) for displaying an image information from the irradiated package (1), wherein said image display device comprises means for checking the contents (1b) of the package (1) for the occurrence or non-occurrence of degradation or the degree of degradation according to the state of dispersion of the package head space in the image information.

4. An inspection apparatus according to claim 3 wherein said image display device (33) comprises a fluorescent image-forming plate (33a), a fluorescent image photographing camera (CCTV) (33b) and a television receiver (33c).

5. An inspection apparatus according to claim 3 wherein said image display device (33) comprises a transmission soft X-ray photographing camera (PbO-TV) (33d) and a television receiver (33c).

6. An inspection apparatus according to claim 3 wherein a sorting device (4) is additionally installed at the downstream end of the second conveyer belt (31) of said main inspecting unit (3) for discharging the package (1), when assessed as defective, in isolation from the package (1) assessed as acceptable.

* * * * *